(12) United States Patent
Hamada

(10) Patent No.: US 6,766,217 B1
(45) Date of Patent: Jul. 20, 2004

(54) METHOD OF MANUFACTURING DENTAL PROSTHESIS, METHOD OF PLACING OBJECT FOR MEASUREMENT AND MEASURING DEVICE

(75) Inventor: Hiroaki Hamada, Tokyo (JP)

(73) Assignee: Kabushiki Kaisya Advance, Tokyo (JP)

( * ) Notice: Subject to any disclaimer, the term of this patent is extended or adjusted under 35 U.S.C. 154(b) by 169 days.

(21) Appl. No.: 10/048,804

(22) PCT Filed: Aug. 2, 2000

(86) PCT No.: PCT/JP00/05185

§ 371 (c)(1),
(2), (4) Date: Jan. 31, 2002

(87) PCT Pub. No.: WO01/08588

PCT Pub. Date: Feb. 8, 2001

(30) Foreign Application Priority Data

Aug. 2, 1999 (JP) ............................................. 11-218875
Jun. 26, 2000 (JP) ........................................ 2000-190529

(51) Int. Cl.[7] ........................... G06F 19/00; A61C 11/00
(52) U.S. Cl. ......................... 700/163; 700/118; 433/213
(58) Field of Search ........................... 700/98, 117, 163, 700/118; 433/202.1, 213, 214

(56) References Cited

U.S. PATENT DOCUMENTS

| | | | |
|---|---|---|---|
| 3,861,044 A | | 1/1975 | Swinson, Jr. |
| 4,166,323 A | | 9/1979 | Maag |
| 4,663,720 A | * | 5/1987 | Duret et al. ................. 700/163 |
| 5,092,022 A | * | 3/1992 | Duret ........................ 29/896.1 |
| 5,184,306 A | * | 2/1993 | Erdman et al. ............. 700/163 |
| 5,257,203 A | | 10/1993 | Riley et al. |
| 5,347,454 A | * | 9/1994 | Mushabac ................... 433/214 |
| 5,549,476 A | | 8/1996 | Stern |
| 5,690,490 A | | 11/1997 | Cannon et al. |
| 5,813,859 A | | 9/1998 | Hajjar et al. |
| 6,049,743 A | * | 4/2000 | Baba ......................... 700/163 |

FOREIGN PATENT DOCUMENTS

| | | |
|---|---|---|
| GB | 2 070 251 A | 9/1981 |
| GB | 2 112 522 A | 7/1983 |
| JP | 57-200144 | 12/1982 |
| JP | 10-277059 | 10/1998 |
| JP | 10-290814 | 11/1998 |
| WO | WO 99/13796 | 3/1999 |

OTHER PUBLICATIONS

International Search Report of PCT/JP00/05185 dated Oct. 26, 2000.
Search Report of Corresponding European Application No. 00 94 9967, dated Feb. 17, 2004.

* cited by examiner

Primary Examiner—Leo Picard
Assistant Examiner—Ryan Jarrett
(74) Attorney, Agent, or Firm—Christie, Parker & Hale, LLP

(57) ABSTRACT

A method of manufacturing a dental prosthesis includes the steps of obtaining shape data of a portion to be prosthetically treated and shape data of a surface condition after it is prosthetically treated, obtaining shape data of a prosthesis from the two shape data sets, obtaining contour data of a portion of the prosthesis contacting a tissue of a living body and appearing outward, and converting the shape data of the prosthesis into a cutting data assuming that a connecting rib is to be connected to the prosthesis at a region appearing outward on the shape data of the prosthesis and substantially not contained in the contour data. Also, the present invention provides a method of placing and object and a measuring device.

2 Claims, 7 Drawing Sheets

METHOD OF MANUFACTURING DENTAL PROSTHESIS, METHOD OF PLACING OBJECT FOR MEASUREMENT AND MEASURING DEVICE

CROSS-REFERENCE TO RELATED APPLICATION

This application claims priority of International patent application No. PCT/JP00/05185, filed on Aug. 2, 2000, which in turns claims priority of Japanese patent Application No. 11-218875, filed on Aug. 2, 1999, and Japanese patent Application No. 2000-190529, filed on Jun. 26, 2000.

TECHNICAL FIELD

The present invention relates to a method of manufacturing a dental prosthesis by utilizing a CAD/CAM device. Also, the present invention relates to a method and device for placing an object so that an objective surface of the object does not overhang when a surface shape of the object is measured.

THE BACKGROUND ART

An attempt has been made to introduce a method of manufacturing a dental prosthesis by using the technique of CAD/CAM into the field of dentistry. In order to obtain a prosthetic shape from the oral cavity, a means for obtaining the prosthetic shape by taking an impression model is effective although it is apparently complicated because it is a method, as a usually adopted dental technical means, by which a precise shape of a dental prosthesis is obtained in a short period of time.

On the other hand, the calculating capacity of a computer has been enhanced and further the price has been reduced, the techniques of CAD/CAM have come into wide use, and manufacturing a dental prosthesis by utilizing the combination of the technique of CAD/CAM has come into practical use.

In this connection, in the case where a dental prosthesis for a small decayed portion of a tooth such as an inlay is manufactured, it is possible to directly mold the decayed portion of the tooth and take it out as a model. However, since the shape of such a dental prosthesis is indefinite, even if the small decayed portion is molded and taken out as a model, it is necessary to mark a contact margin portion coming into contact with a tooth and also it is necessary to mark a portion which becomes a surface of the tooth. Since the dental prosthesis concerned is very small and its shape is indefinite, it is complicated to directly measure the surface of the dental prosthesis.

As a method of making a three-dimensional measurement of an object, there are provided a laser beam method, a contact method, a gray scale method, a moire method and so forth. However, when the measurement is made in one direction, if the object has an overhang portion, it is impossible to measure a portion shaded by the overhang portion. In this case, the overhang portion means a portion which protrudes in a direction perpendicular to the measuring direction.

In order to obtain information which cannot be obtained from the portion shaded by the overhang portion, there is provided a method in which multiple axes are manually or automatically controlled. However, actually, the adjusting axes, ranges and units are limited. Therefore, it is necessary to place the object at a position and also it is necessary to place the object in a direction so that the object can be measured under the above conditions. This important work must be manually conducted, which is complicated and difficult.

In the case of using a measurement device, the degree of freedom of which is high, the accuracy is usually low. In the case of using a measurement device, both the accuracy and the degree of freedom of which are high, the cost is increased.

In the case where an object is measured in one direction, it is necessary to place the object so that an overhang portion cannot be created. In this case, the overhang portion means a portion located at the rear of a protruding portion in a direction perpendicular to the measuring direction. However, in the case of an object, the shape of which is horizontal with respect to the measuring direction, or the shape of which is oblique and is close to the horizontal shape, it is difficult to manually place the object so that the overhang portion cannot be created. It can be considered that even if the overhang portion is created, it is impossible to discriminate the overhang portion from other portions and a measurement is executed as it is.

SUMMARY OF THE INVENTION

It is an object of the present invention to provide a method of manufacturing a dental prosthesis capable of providing a dental prosthesis, the shape of which is indefinite, with high accuracy.

It is another object of the present invention to provide a method of placing an object for measurement and a measuring device capable of accurately measuring an object to be measured which may have an overhang portion.

In order to accomplish the above object, the present invention provides a method of obtaining shape measuring data of a dental prosthesis while consideration is given to machining the dental prosthesis by CAD/CAM.

That is, first, data of a natural tooth having a decayed portion are obtained from an impression model. After that, a temporary filler is charged into this impression model, and data of the entire tooth after prosthetic treatment are obtained. Then, these two sets of data are differentially synthesized in the same coordinate space so as to obtain a shape of the dental prosthesis.

According to this method, the calculation of a difference can be executed while attaching an importance to one of three directions, and the amount of calculation can be reduced. That is, the surface after the completion of prosthetic treatment is smooth in many cases. In this case, it is possible that the surface is assumed to be on a plane formed by axes of X and Y. On the other hand, data of the decayed portion may be assumed to be data in the direction of Z-axis. Therefore, it is possible to concentrate the calculation upon one coordinate in the three dimensional coordinates.

Further, since the data are based on the surface data of the tooth which has been subjected to dental prosthetic treatment, the margin line and the surface portion of the tooth can be easily recognized.

Due to the foregoing, when the dental prosthesis is machined, a position of the connector for connecting the machining device with the machining block can be automatically grasped, and a space in which adhesive is coated can be easily formed.

When the connector is mounted on the surface, the dental prosthesis and the natural tooth can be connected to each other without being affected by the connector. The remnants produced when the connecting rib and the dental prosthesis are separated from each other after the completion of machining can be easily cut off and adjusted.

The present invention provides a method of forming data used when a dental prosthesis, the shape of which is indefinite, such as an inlay is measured and the dental prosthesis concerned is machined. On the assumption that the data are formed, an organized decayed tooth portion, into which a dental prosthesis is introduced, is formed.

A model of a shape of a decayed tooth portion is made of plaster by a conventional method.

Data of a surface shape of the model are obtained.

Concerning the means for obtaining the surface shape data, there are provided a means for obtaining digital data by contact scanning on the surface conducted by a contact probe, an optical means in which laser beams are used, and a means for obtaining digital data by using ultrasonic waves or photographs. In order to obtain highly accurate surface shape data, it is preferable to adopt a means in which the contact probe is used.

A decayed portion of the decayed tooth portion model is prosthetically treated, and a tooth shape model having a surface after the completion of prosthetic treatment is obtained.

Surface data of the tooth shape model are obtained by the above method.

Measuring a tooth model of a predetermined size stably as described above is easier than directly measuring an indefinite dental prosthesis shape.

Three dimensional coordinates are set on the basis of the surface data concerned. Alternatively, the surface data are converted onto the common three dimensional coordinates.

In this connection, the surface data are not necessarily provided with a flatness property in a portion to be prosthetically treated. Further, it is not necessary for the surface data to have a flatness property in a portion to be prosthetically treated.

The decayed tooth shape portion model is converted into three dimensional data so that the model can be matched with the surface data from the positional viewpoint. In this case, a portion which changes from a position at which both data coincide with each other becomes boundary data (margin line) between the natural tooth and the dental prosthesis, and data showing the dental prosthesis shape is formed. The change may be determined by whether the data exist or not. However, since errors may be caused in the values in some cases, it is possible to provide a process in which it is judged that the dental prosthesis portion exists when a change is caused in a unit distance and this change continues by a predetermined number of times.

Plane coordinates caused by the surface data on the three-dimensional coordinates are made into a unit matrix, and a difference between the surface data corresponding to it and the surface profile data of a decayed portion for each unit is calculated, or a summation of the surface data corresponding to it and the surface profile data of a decayed portion for each unit is calculated. In this way, numeric values necessary for machining are obtained.

When the thickness of a dental prosthesis in the periphery of a boundary portion is measured and the measured thickness is not sufficiently large, this portion may be erased and the boundary portion may be corrected.

This correction may be arbitrarily visually made by a display, in the case of connection of a dental prosthesis shape, virtually displayed on a display according to the above data and a decayed tooth portion shape. Alternatively, this correction may be made by process in which every portion is equally erased.

A correction is made according to the boundary line concerned so that a space (offset) in which adhesive is coated in the periphery of the dental prosthesis data can be provided.

A connecting position of a rib for machining is determined from the surface data. It is preferable that the connecting position concerned is determined so that it is not contacted with the margin line. Even if the connecting position concerned is contacted with the margin line, it is preferable to determine the connecting position so that the contact length can be minimized.

In the method of placing an object for measurement and the measuring device of the present invention, while the system is not greatly changed, the same state as that of measurement is adopted when the object is placed so that an overhang portion cannot be created. In this way, the object is placed and fixed. Due to the foregoing, an essential and important work of measurement, which is visually and manually conducted in the prior art or conducted by a highly sophisticated system, can be simply and positively conducted. As a measurement system, it is sufficient that a limited function is provided. Therefore, it is possible to put it into a wide use and further the cost can be reduced.

In the present invention, in the case where a measurement object placing section is set to be a horizontal plane, the measurement object is moved so that a vertical face of the measurement object can coincide with a vertical side of an adjusting member and this state can be fixed.

For example, the side of the adjusting member is contacted with the vertical face of an object to be measured and fixed by a holder so that the state can be temporarily held. An example of the holder is a jig by which a changed state of the measurement object can be fixed as it is when the adjusting member and the vertical face coincide with each other.

The adjusting member can be substituted by a probe for measuring the profile of the measurement object when the probe itself has such a vertical face. In this connection, when at least the side of the adjusting member or the face originated from the side of the probe can be kept vertical or adjusted to be vertical, after the measurement object has been held on the side of the probe, the state may be adjusted so that the measurement object placing section can be placed with respect to the face of the measurement object.

In this connection, the present invention is effectively utilized for a measuring and machining device for a dental prosthesis such as an artificial root of a tooth having a large number of indefinite measurement objects and further having a large number of vertical and horizontal portions.

BRIEF DESCRIPTION OF THE DRAWINGS

An embodiment of the present invention will be explained by referring to the appended drawings, in which.

BEST MODE FOR CARRYING OUT THE INVENTION

Figure 1:
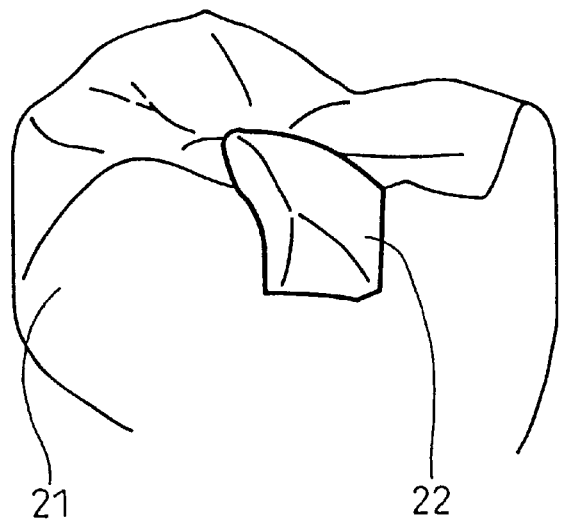
FIG. 1 is a view showing an example of a tooth having a decayed portion.

First, a model of the tooth 21 is made which has a surface shape having a decayed portion 22 as shown in FIG. 1.

Concerning the method of making this model, it is possible to apply a well known technique of dental treatment in which an impression material having a hardening property is used.

Next, the surface shape of this tooth model is digitized. In order to digitize the surface shape of this tooth model, the surface shape is converted into surface shape data by a contact or non-contact method using a CAD/CAM device. A range of the tooth model to be digitized may include at least a periphery of the decayed portion.

Figure 2:
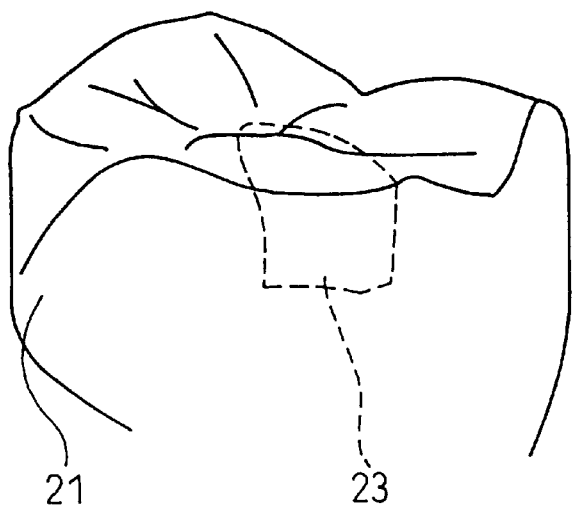
FIG. 2 is a view showing an example of a tooth model in which the tooth model shown in FIG. 1 is temporarily prosthetically treated.

Next, this tooth model is temporarily prosthetically treated, so that a complete model shown in FIG. 2, in which the prosthesis treatment has been completed, is made. After that, the surface shape of this complete model is digitized. Reference numeral 23 is a portion which has been temporarily prosthetically treated.

When any image data are restored on an image plane of a computer, it is possible to display the shapes shown in FIGS. 1 and 2 on a display or printer. Therefore, in order to make the explanation easy when a composite calculation is made, all data are shown in the form of an image in FIG. 3 and after that.

Next, these data are converted into the same coordinate space. As an example of the coordinates, three-dimensional coordinates are shown. In order to make the calculation easy, the surface shape is turned inside out.

In this connection, in some cases, the calculation may be made without inverting data in the direction of the Z-axis. When the reference surface is on the coordinates of Y-Z axes, the calculation may be made around the X-axis. That is, the calculation may be appropriately selected.

Figure 3:
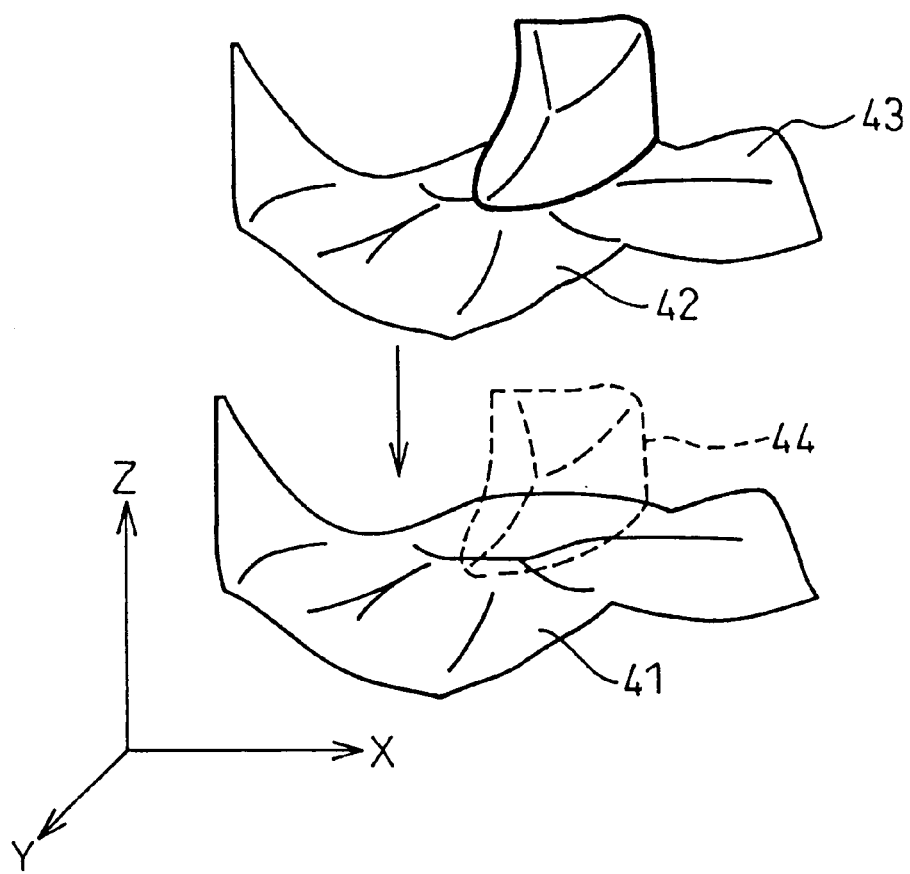
FIG. 3 is a view showing surface data of a tooth obtained from the example shown in FIG. 1 and also showing surface data of a temporary dental prosthesis obtained from the example shown in FIG. 2.

In FIG. 3, reference numeral 41 represents surface data of a temporary dental prosthesis, which has been temporarily prosthetically treated, in which the data obtained from the example shown in FIG. 2 are inverted. Reference numeral 42 represents surface data of a tooth having a decayed portion 43 in which the data obtained from the example shown in FIG. 1 are inverted. The surface data 42 of a tooth and the surface data 41 of a temporary dental prosthesis are put on each other in the direction of Z-axis under the condition that the surface data 42 of the tooth and the surface data 41 of the temporary dental prosthesis are made to agree with the XY coordinates.

As a result of putting the data together, the decayed portion 44 is shown being protruded. When the data are subjected to a differential calculation, absolute values can be obtained, and data of Z-axis coordinates can be obtained with respect to the X-Y coordinates.

The two-dimensional coordinates on the X-Y axis are subjected to unit division ((x1, y1)(x2, y2) . . . (xn, yn)). When data of the Z-axis with respect to the X-Y coordinates data for each unit are obtained, the data can be processed.

The accuracy of restoration is changed by a quantity of unit data in the X-Y coordinates data. When a sharp change is required, the X-Y unit coordinates are divided into minute portions, and when a gentle change is required, the unit coordinates are increased. Due to the foregoing, a quantity of calculation can be adjusted, and the processing time can be shortened, in some cases.

Figure 4A:
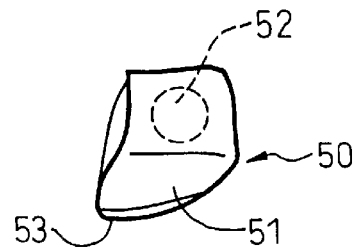
FIG. 4A is a view showing shape data of a dental prosthesis.

When these differential data and coordinates data are obtained, it becomes possible to obtain the shape data 50 of a dental prosthesis shown in FIG. 4A. In this case, as can be seen in FIG. 3, the data 53 showing a margin in the periphery of the decayed portion can be easily detected, and at the same time the surface data 51 (exposed surface portion) of the dental prosthesis can be easily shown.

Reference numeral 52 is a rib attaching portion to which a rib is attached when the machining block is set at the machining device. This rib attaching portion can be easily set. It is preferable that the rib attaching portion 52 is not concerned in the margin. The margin line 53 is a portion where the tooth and the dental prosthesis are contacted with each other. In order to prevent the occurrence of a secondary decay, the tooth and the dental prosthesis must be closely contacted with each other. Therefore, the accuracy of the margin line 53 must be high.

The rib attaching portion 52 is a portion where the final finishing is executed when the dental prosthesis is machined. In many cases, the rib attaching portion 52 is made by simple cutting. Therefore, a burr tends to be created in the rib attaching portion 52. Accordingly, it is not appropriate for the margin line 53 to be machined in the rib attaching portion 52. For the above reasons, it is preferable that the rib attaching portion 52 is formed in a portion which is exposed to the surface of the dental prosthesis and not contacted with the margin line 53. In the present invention, the portion which is exposed to the surface can be easily determined. Therefore, the rib attaching portion 52 can be very easily determined. Even in the case where the portion which is exposed to the surface is smaller than the rib attaching portion 52, the portion 52 which does not overlap the margin line 53 can be easily selected by the optimized calculation.

4B is a view showing a state in which these dental prosthesis data are put on the block for machining. Reference numeral 62 is a rib, which is used for connecting with the machining device. Reference numeral 61 is an auxiliary portion. It is preferable that this auxiliary portion 61 is made of material capable of being cut and ground in the same manner as that of the block for machining. When this auxiliary portion 61 is made of material capable of being cut and ground, it possible for a milling cutter to enter this auxiliary portion 61 so that the peripheral portion of the rib can be easily machined.

Figure 4B:
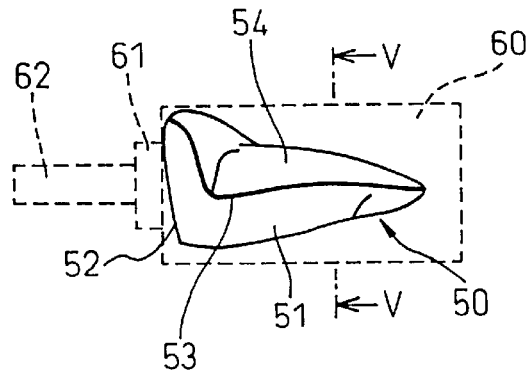
FIG. 4B is a view showing shape data of a dental prosthesis shown together with a block for machining.

Reference numeral 50 represents data of a dental prosthesis, and reference numeral 60 represents data of a block for machining. A block, the shape of which is shown by the machining block data 60, is formed into the dental prosthesis shape 50 by grinding and cutting. In this case of dental prosthesis treatment, in order to join the decayed portion, an adhesive is coated. Therefore, the side of the dental prosthesis is shaved somewhat deep. That is, what is called an offset treatment is conducted. A case of the offset treatment is shown in FIG. 5, which is a sectional view taken on line V—V in FIG. 4B.

Figure 5:
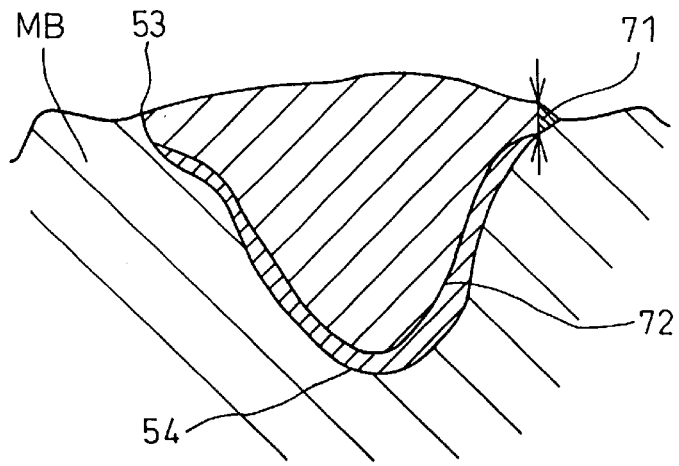
FIG. 5 is a sectional view showing data of a dental prosthesis, taken along the line V—V in FIG. 4B.

In FIG. 5, reference numeral 72 is an offset line. The offset line 72 is offset by a constant distance from the line 54 of the dental prosthesis. However, since the margin line 53 comes close to the offset line 72, an offset value becomes 0 in this portion.

As shown by the reference numeral 71 in FIG. 5, in the periphery of the margin line, a portion, the thickness of which is insufficient, are caused continuously or discontinuously in some cases. Since this portion tends to crack in the case of chewing, it is preferable to erase this portion previously. Consequently, for the purpose of erasing this portion, the mechanical strength of which is insufficient, the margin line is corrected.

In the case where the thickness changes discontinuously, it is preferable that the correcting work is visually conducted. In the case where the thickness changes continuously, the data of the portion is automatically erased and corrected.

An aim of occurrence of crack changes, depending upon materials of metal, ceramics and so forth, and the materials are to be appropriately selected.

Figure 6:
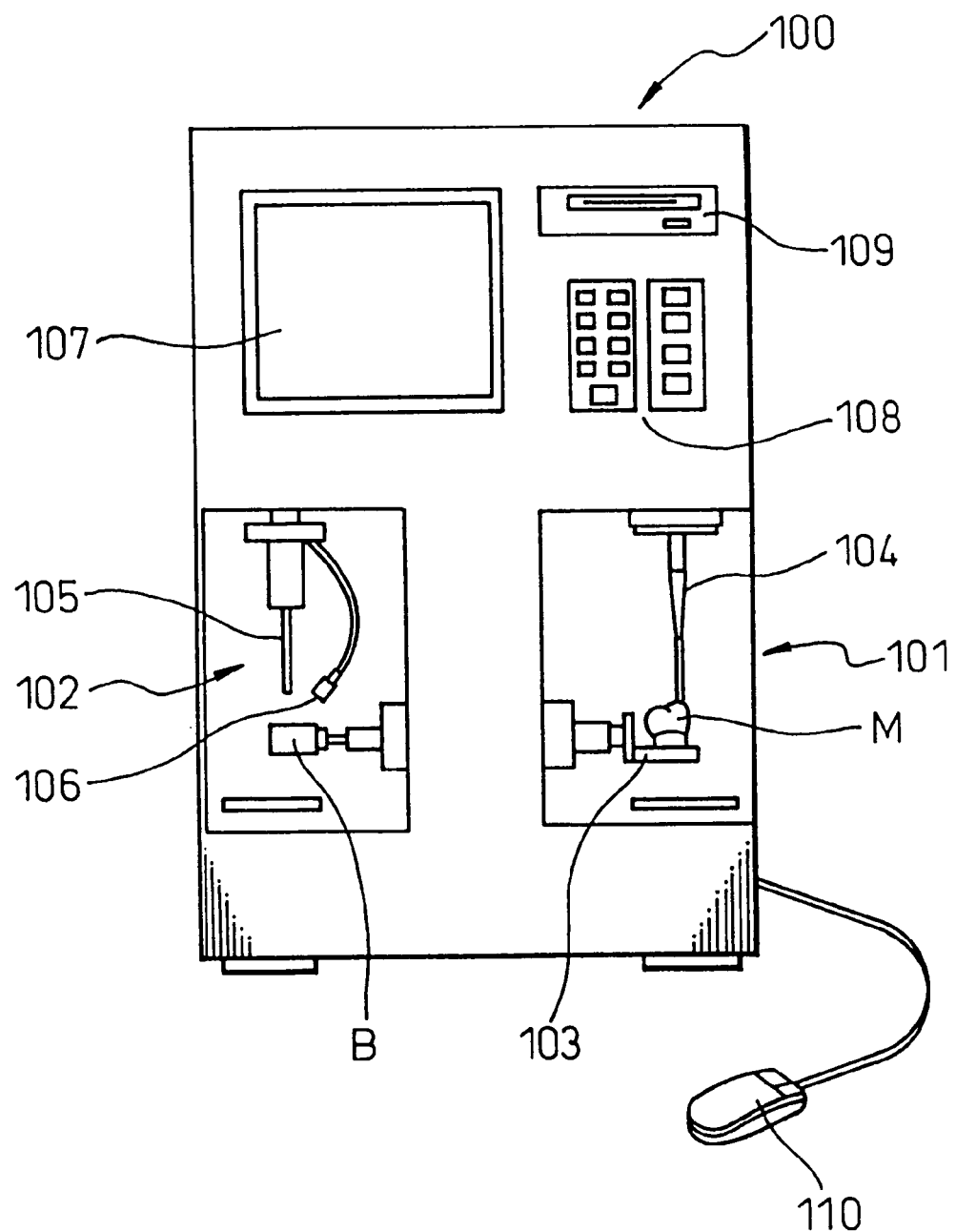
FIG. 6 is a view showing a machining device used for the present invention.

Referring to FIG. 6, an example of the device will be explained below which houses software for conducting a series of machining described above and conducts measuring and machining. In the main body 100, the measuring section 101 and the machining section 102 are arranged symmetrically with each other. In an upper portion of the device, there are provided a monitor 107 and a driver 109 used for reading and writing of an external memory means such a floppy disk. Reference numeral 108 is a simple operation panel. When an operator presses buttons, various parameters can be inputted into the operation panel 108.

It is preferable that this portion, in which the monitor 107 and the driver 109 are accommodated, is formed into a common computer portion. In this case, the mouse is attached in some cases so that a detailed setting operation can be made on the monitor 107. Although not described in the drawing, a keyboard is attached in some cases.

In the measuring section 101, reference numeral 104 is a contact probe. When a forward end of the probe 104 comes into contact with the surface of a dental prosthesis, a change in the probe can be turned into data. Reference numeral 103 is a measurement mount on which an object to be measured is mounted only one side of the measurement mount 103 can be used, however, the measurement mount 103 may be rotated so that both sides of the measurement mount 103 can be used. Reference mark M is a model of a tooth. The model shown in FIGS. 1 and 2, which has been previously formed, is mounted on the measurement mount 103.

In the machining section 102, reference numeral 105 is a machining mill. The machining mill 105 can be moved up and down. Further, the machining mill 105 can be moved to the right and left. In the machining section 102, reference numeral 106 is a nozzle for injecting a washing solution. This nozzle 106 is arranged being linked with the machining section 102. When the washing solution is injected, chips can be washed off in the process of grinding and cutting. The washing solution washes away chips produced in the process of grinding and cutting at any time. Further, the washing solution cools an object to be machined.

Reference character B is a block to be machined, which is made of feldspar, other ceramics, titanium and other metals which are capable of being cut and ground so that the block B can be formed into a dental prosthesis. The block B to be machined can be rotated round the rib 62, so that both sides of the block B can be machined.

In this machining device, a commonly used computer is housed, and processing of CAD/CAM is conducted by the computer. Therefore, this machining device can be widely and effectively used. Further, this machining device is integrated into one body and formed compactly.

As described above in detail, according to the present invention, it is possible to accurately measure an indefinite dental prosthesis such as an inlay, the shape of which is precise. Further, it is possible to convert the measured data into data appropriately used for machining.

Figure 7A:
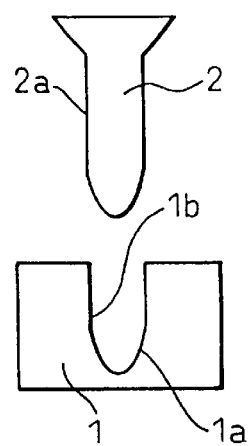
FIGS. 7A to 7E are views showing an embodiment of the method of placing an object for measurement and the measurement device of the present invention.

FIGS. 7A to 7E are views showing an embodiment of a method of placing an object for measurement and a measuring device. An example is explained in which the object 1 to be measured having a vertical hollow portion is measured. As shown in FIG. 7A, the appearance of the object 1 to be measured is a hollow contour 1a. The object 1 to be measured has a vertical face 1b which is arranged in the longitudinal direction. The positioning jig 2, the shape of which is the same as that of the measuring probe 5, is prepared. The positioning jig 2 has at least a portion 2a which agrees with the vertical face 1b of the object 1 to be measured.

Figure 7B:
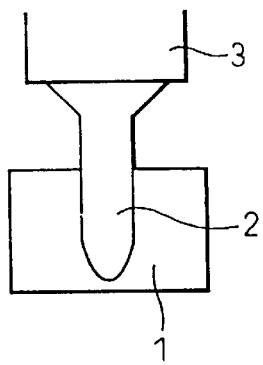

As shown in FIG. 7B, the positioning jig 2 is inserted into the hollow 1a of the object 1 to be measured. Then, the positioning jig 2 is fixed so that a hangover portion cannot be created in the direction of the jig. In the drawing, the shape of the positioning jig 2 is the same as that of the object 1 to be measured. However, the present invention is not limited to the above specific embodiment, and the following arrangements may be adopted. The positioning jig 2 has at least a portion which agrees with a vertical face of the object 1 to be measured, and also the positioning jig 2 has at least a portion which agrees with a horizontal face of the object 1 to be measured. The position of the object 1 to be measured can be adjusted in such a manner that the object 1 is lifted up or moved upward by being linked with the positioning jig 2, so that the vertical face and the horizontal face of the positioning jig can be made to agree with the vertical face and the horizontal face of the object 1 to be measured.

Figure 7C:
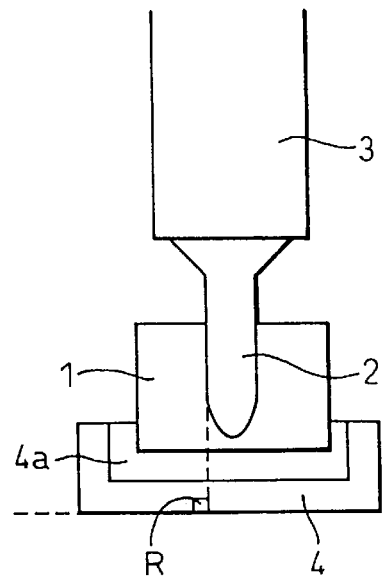

The positioning jig 2 is attached to the measuring device 3, and the measuring device 3 is operated and moved to a position, the height of which is close to the height of measuring the object. Under the above condition, the object 1 to be measured is fixed to the jig 4 for fixing the object to be measured (FIG. 7C).

At this time, the jig 4 for fixing the object 1 to be measured and the face 1b of the object 1 to be measured are set perpendicular to each other. This perpendicular relation of the jig 4 with the face 1b of the object 1 to be measured is expressed by reference mark R. The jig 4 for fixing the object to be measured is provided with an adjusting section 4a for arranging the vertical portion with accuracy. When the object 1 to be measured is vertically arranged in this adjusting section 4a, the object 1 to be measured is fixed as it is. Therefore, this adjusting section 4a is provided with a pushing and fixing tool.

Figure 7D:
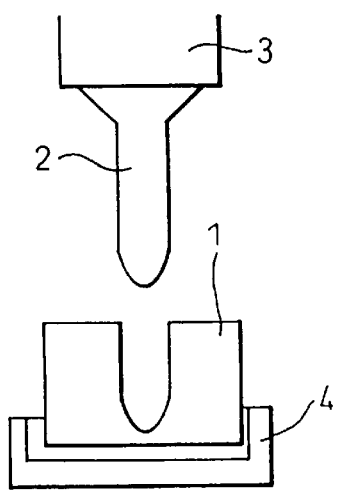

Next, the positioning jig 2 is removed from the object 1 to be measured while the object 1 to be measured is being kept stationary so that it cannot move from the fixing jig 4 (FIG. 7D).

Figure 7E:
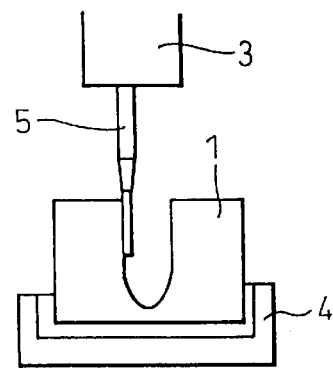

Under the above condition, no overhang portion is created in the hollow portion 1a of the object 1 to be measured when the object 1 is viewed from the positioning jig 2, that is, the hollow portion 1a of the object 1 can be measured by the measuring probe 5. Therefore, the positioning jig 2 is detached from the measuring device 3, and the measuring probe 5 is attached to the measuring device 3 so as to conduct a measurement of the hollow portion 1a of the object 1 to be measured (FIG. 7E).

Figure 8A:
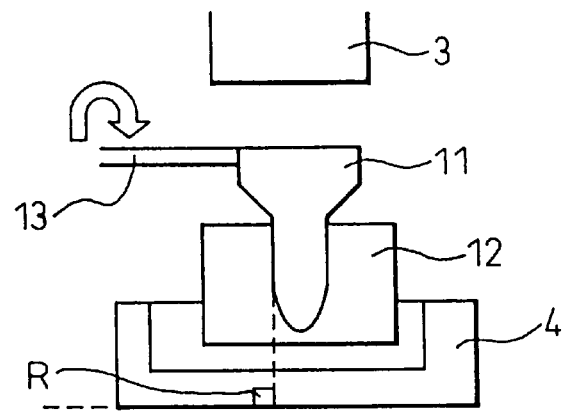
FIGS. 8A and 8 are views showing an example of measuring a convex measurement object.
Figure 8B:
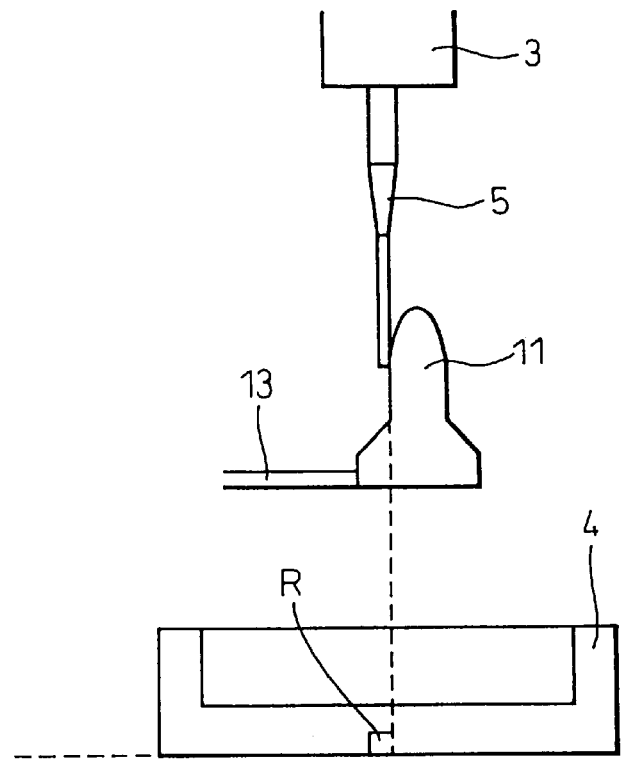

Further, an example of measuring an object 11, the shape of which is convex, is shown in FIGS. 8A and 8B. In FIG. 8A, first, the member 21 having a concave shape is made of impression material and positioned in the same manner as that described above. That is, the member 21 having the concave shape shown in FIG. 8A is set in the same state as that of the object 1 to be measured shown in FIG. 7C.

This member 12 having the concave shape is inserted into the object 11 to be measured, the shape of which is convex. In this state, the rotary shaft 13 is connected to the object 11 to be measured.

The rotary shaft 13 is accurately rotated by 180° to the measuring direction, and the measuring probe 5 is connected with the measuring device 3. Under the above condition, the surface shape of the object 11 to be measured is measured (FIG. 8B).

Figure 9:
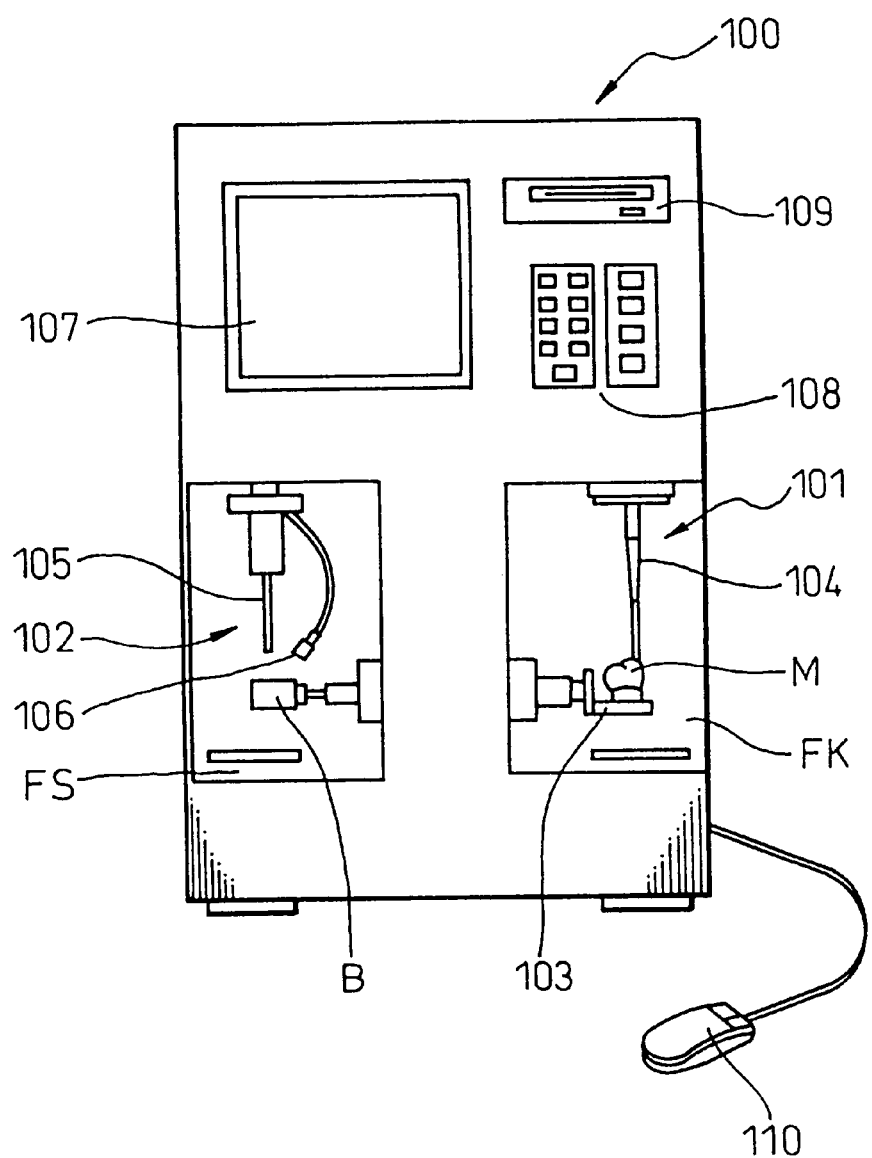
FIG. 9 is a view showing an example of a machining device.

FIG. 9 is an example of the measuring and machining device used for dentistry to which the present invention can be preferably applied. This measuring and machining device is similar to the machining device shown in FIG. 6.

Reference numeral 100 is a body of a measuring and cutting device used for dentistry. This measuring and cutting device used for dentistry includes: a section for measuring a shape of an object; and a cutting section for processing shape data obtained in the measurement and for cutting a block made of a prosthesis material according to the shape data.

Reference numeral 101 is a measuring section, in which the model M is set on the measuring mount 103 which is manually or automatically rotated or slid. In this case, it is preferable that the measuring mount 103 is manually or automatically slid. In this measuring section 101, the measuring probe 104 is contacted with this model M, and the surface shape of the model M is measured according to a displacement of the measuring probe 104.

Reference numeral 102 is a cutting section (machining section). In the cutting section 102, there is provided a rotary drill 105 capable of sliding up and down and also sliding to the right and left. In the cutting section 102, the block B, which is made of feldspar, ceramics such as hydroxyapatite or metal such as titanium capable of being used as a dental prosthesis material, is supported. When necessary, the cutting section 102 includes a support mount 111 capable of rotating or sliding by manual or automatic operation.

Further, there is provided a nozzle 106 from which water is outputted for washing away chips, which are produced when the rotary drill 105 comes into contact with the block B and grinds and cuts it, from the block B. This nozzle 106 is arranged being linked with the rotary drill 105.

Both the measuring section 101 and the cutting section 102 include transparent cover sections FK, FS, which can be opened in the vertical or traverse direction, for preventing the chips from scattering and also for protecting the measuring section.

Reference numeral 107 is a monitor which is used for monitoring the states of measuring and cutting when the measuring and machining device is operated. Reference numeral 108 represents panel switches which are pressed for adjusting the measuring and cutting motion. Reference numeral 109 is a drive unit which is used when data are read from the recording medium or written into recording medium when necessary.

The recording medium comprises a floppy disk, MO, CD-ROM and so forth. This recording medium is appropriately selected in accordance with the drive unit. Reference numeral 110 is a mouse. The mouse 110 is used when an icon is indicated and executed with a pointer which is linked with a movement of the mouse so that an image can be formed on the monitor. In some cases, the mouse can be more easily operated than the panel switches 108.

The main body houses at least a commonly used computer. This computer conducts a compound calculation of the measured data. Further, this computer makes the device conduct a measuring motion by utilizing the well known technology of CAD. The present invention mainly covers a process to be conducted before a measurement. A program based on this process is executed, and it is preferable that the program based on this process is temporarily or steadily stored.

It is more preferable that the main body houses another computer so that the drive of the rotary drill for cutting can be controlled.

In this connection, according to the arrangement of the device concerned, it is possible to conduct copy machining in which the measuring and the cutting operation are simultaneously carried out by being linked with each other.

As described in detail above, according to the present invention, the following effects can be provided. It is possible to provide an object to be measured, which is set in an accurately vertical or horizontal condition, by a simple method. Further, it is possible to obtain precise information of the shape in the periphery of the object to be measured.

What is claimed is:

1. A method of manufacturing a dental prosthesis comprising the steps of:

obtaining first shape data of a portion of a tooth to be prosthetically treated and second shape data of a surface condition of an impression model of the portion of a tooth to be prosthetically treated after the impression model is prosthetically treated;

obtaining third shape data of a prosthesis from the first shape data and the second shape data;

obtaining boundary data of the third shape data of a prosthesis at which the prosthesis would contact the tooth; and converting the third shape data of a prosthesis into cutting data for cutting a block to be machined, wherein, a connecting rib is connected to the prosthesis at a protruding region on the third shape data of the prosthesis and is substantially outside the boundary data;

wherein the first shape data and the second shape data are converted into respective three-dimensional first shape data and three-dimensional second shape data, two dimensions being reference dimensions for comparison of third dimension data of the three-dimensional first shape data and the third dimension data of the three-dimensional second shape data; and wherein data changes from the comparison are used to obtain the third shape data of a prosthesis.

2. The method of manufacturing a dental prosthesis according to claim 1, wherein the three-dimensional first shape data and the three-dimensional second shape data are substantially superimposed on each other.

* * * * *

UNITED STATES PATENT AND TRADEMARK OFFICE
CERTIFICATE OF CORRECTION

PATENT NO. : 6,766,217 B1 Page 1 of 1
DATED : July 20, 2004
INVENTOR(S) : Hamada It is certified that error appears in the above-identified patent and that said Letters Patent is hereby corrected as shown below:

Title page,
Item [54], Title, replace title with -- METHOD OF MANUFACTURING DENTAL PROSTHESIS BY COMPARING TOOTH SHAPE DATA TO IMPRESSION MODEL SHAPE DATA --
Item [56], References Cited, OTHER PUBLICATIONS, insert -- Corresponding EPO Application Search Report dated 05-13-2003 --
Item [57], ABSTRACT,
Line 12, delete "placing and object", insert -- placing an object --

Signed and Sealed this

Twenty-first Day of June, 2005

JON W. DUDAS
*Director of the United States Patent and Trademark Office*